(12) United States Patent
Allmendinger et al.

(10) Patent No.: US 11,517,281 B2
(45) Date of Patent: Dec. 6, 2022

(54) METHOD FOR GENERATING IMAGE DATA, COMPUTED TOMOGRAPHY SYSTEM, AND COMPUTER PROGRAM PRODUCT

(71) Applicant: Siemens Healthcare GmbH, Erlangen (DE)

(72) Inventors: Thomas Allmendinger, Forchheim (DE); Christian Hofmann, Erlangen (DE); Harald Schoendube, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 275 days.

(21) Appl. No.: 16/872,434

(22) Filed: May 12, 2020

(65) Prior Publication Data

US 2020/0367847 A1 Nov. 26, 2020

(30) Foreign Application Priority Data

May 21, 2019 (DE) .......................... 102019207419.7

(51) Int. Cl.
*A61B 6/00* (2006.01)
*G06T 11/00* (2006.01)

(52) U.S. Cl.
CPC .......... *A61B 6/5264* (2013.01); *G06T 11/003* (2013.01); *G06T 2210/41* (2013.01)

(58) Field of Classification Search
None
See application file for complete search history.

(56) References Cited

U.S. PATENT DOCUMENTS

| 5,799,059 | A | 8/1998 | Stembridge | |
|---|---|---|---|---|
| 6,674,834 | B1 * | 1/2004 | Acharya | A61B 6/583 |
| | | | | 378/207 |
| 8,186,880 | B1 * | 5/2012 | Arnold | A61B 6/032 |
| | | | | 378/207 |

(Continued)

FOREIGN PATENT DOCUMENTS

DE 102016208123 A1 9/2017

OTHER PUBLICATIONS

German Office Action for German Patent Application No. 102019207419.7 dated Mar. 9, 2020.

*Primary Examiner* — Hoon K Song
(74) *Attorney, Agent, or Firm* — Harness, Dickey & Pierce, P.L.C.

(57) ABSTRACT

A method is for generating image data of an examination object via a computed tomography system including a data processing unit; an X-ray radiation source and an X-ray radiation detector suspended on a support and mounted to be rotatable about a z-axis; and an examination table for supporting the examination object and a reference object arranged in a fixed position relative to the examination table. The method includes generating a raw data set by displacing the X-ray radiation source and the X-ray radiation detector relative to the examination object. During generation of the raw data set, at least one part of the examination object is sampled together with at least one part of the reference object. The sampling of the at least one part of the reference object is used to compensate at least in part for the influence of movement errors during the displacement.

23 Claims, 2 Drawing Sheets

(56) References Cited

U.S. PATENT DOCUMENTS

2008/0240364 A1* 10/2008 Main .................... A61N 5/1048
                                                      250/252.1
2017/0325763 A1   11/2017 Hoernig et al.
2018/0242944 A1*   8/2018 Uber, III .............. A61B 5/0035
2019/0261940 A1*   8/2019 Son ....................... A61B 6/461

* cited by examiner

METHOD FOR GENERATING IMAGE DATA, COMPUTED TOMOGRAPHY SYSTEM, AND COMPUTER PROGRAM PRODUCT

PRIORITY STATEMENT

The present application hereby claims priority under 35 U.S.C. § 119 to German patent application number DE 102019207419.7 filed May 21, 2019, the entire contents of which are hereby incorporated herein by reference.

FIELD

Embodiments of the invention generally relate to a method for generating image data of an examination object via a computed tomography system; and to a computed tomography system and a computer program product.

BACKGROUND

Computed tomography systems typically have what is known as a gantry with an X-ray radiation source and with an X-ray radiation detector and, as is known, are used for the examination of objects via X-ray radiation. In this process, a corresponding object is examined in most cases via what is known as a spiral scan or spiral sampling and, during the course of such a spiral scan, a raw data set is generated, on the basis of which image data, such as sectional images of the object, can subsequently be generated or calculated. During the generation of a corresponding raw data set, an examination volume of an examination object is subdivided via a grid into what are known as voxels or 3D pixels, and each voxel is assigned a type of attenuation value that is characteristic of the attenuation of X-ray radiation when passed through by the corresponding voxel.

The calculation or assignment of corresponding attenuation values here is conditional upon the knowledge of the relative position of the X-ray radiation source and the X-ray radiation detector relative to the examination volume at any point in time during the corresponding spiral scan, and the more precisely the relative positions are known at the different points in time, the higher the image quality that can be achieved for the image data, for example the sectional images of the object.

In practice, it is usual when calculating the attenuation values to assume that, during each spiral scan, the X-ray radiation detector on the one hand and the X-ray radiation source on the other hand travel along an ideal spiral path about a z-axis or z-direction at a constant speed which is determined by the pitch factor, which can be selected before the examination and can therefore be predetermined in a variable manner. By way of a complex movement mechanism, this idealized movement is then completed as far as possible, so that the required relative positions closely approximate the real relative positions. Possible movement errors, in other words deviations of the real relative positions from the required relative positions along the ideal spiral path, are not usually detected on the basis of measurements and accordingly are not taken into consideration when calculating the attenuation values.

In order to realize a movement mechanism which is as precise as possible, in many cases the gantry on the one hand and an examination table or at least a base of the examination table on the other hand are arranged during installation in a fixed position relative to one another and in a fixed alignment relative to one another in an examination room and in addition securely anchored for example to the floor of the examination room. For the required relative movements, in such cases a tabletop of the examination table is then typically displaceable linearly in the z-direction by way of a positively driven operation, and the X-ray radiation detector and the X-ray radiation source are suspended in the gantry and are rotatable via a positively driven operation.

Also known are what are referred to as sliding gantry systems, which differ from the system described above in that a linear movement in or against the z-direction is not realized via the examination table and its tabletop but instead via the gantry, which is supported for this purpose on a securely mounted rail system such that it can be displaced in the z-direction.

In both cases, there is a certain (location) coupling between the examination table and the gantry, as a result of which freedom of movement for relative movements between the examination table, on which an examination object is supported, and the X-ray radiation source and X-ray radiation detector, which are suspended in the gantry, is restricted and/or as a result of which a shared (location) reference system is predetermined. Such a coupling reduces possible movement errors, in other words deviations of the real relative positions from the required relative positions along the ideal spiral path, and thus increases the achievable image quality.

The application DE 10 2016 208 123 A1, the entire contents of which are hereby incorporated herein by reference, furthermore discloses an arrangement having a gantry of a medical imaging device and an omnidirectional chassis for moving the arrangement relative to a base.

SUMMARY

Embodiments of the invention specifies an advantageous method for generating image data, an advantageous computed tomography system, and an advantageous computer program product.

Embodiments of the invention are directed to a method, a computed tomography system, and a computer program product. Preferred developments are contained in the back-referenced claims. The advantages listed in relation to the method and preferred embodiments can be applied analogously to the computed tomography system and/or the computer program product and vice versa.

In at least one embodiment, the method is used for generating image data of an examination object, for example a patient, via a computed tomography system having a data processing unit, which computed tomography system has an X-ray radiation source and an X-ray radiation detector, which are suspended on a support and are mounted such that they are rotatable about a z-axis, and which computed tomography system has an examination table or patient table for supporting the examination object as well as a reference object arranged in a fixed position relative to the examination table.

In at least one embodiment, a method regarding an examination object, uses a computed tomography system including a processor, an X-ray radiation source and an X-ray radiation detector suspended on a support and mounted to be rotatable about a z-axis, and an examination table to support the examination object and a reference object arranged in a fixed position relative to the examination table, the method comprising:

generating a raw data set by displacing the X-ray radiation source and the X-ray radiation detector, relative to the examination object;

sampling via X-ray radiation, during the generating of the raw data set, at least one part of the examination object, together with at least one part of the reference object; and compensating at least in part for an influence of movement errors, using the sampling of the at least one part of the reference object, during the displacing of the X-ray radiation source and the X-ray radiation detector relative to the examination object.

In at least one embodiment, the method further comprises:
comparing data from the raw data set or data derived from the raw data set with trained data;
determining, based upon the comparing, at least one correction variable; and
generating image data of the examination object using the at least one correction variable determined.

In at least one embodiment, a computed tomography system, comprises:
an X-ray radiation source and an X-ray radiation detector, suspended on a support and mounted to be rotatable about a z-axis;
an examination table to support an examination object and a reference object, arranged in a fixed position relative to the examination table; and a data processor configured to:
  generate a raw data set upon displacing the X-ray radiation source and the X-ray radiation detector, relative to the examination object;
  sample, via X-ray radiation, during generating of the raw data set, at least one part of the examination object, together with at least one part of the reference object; and
  compensate at least in part for an influence of movement errors, using the sampling of the at least one part of the reference object, during the displacing of the X-ray radiation source and the X-ray radiation detector relative to the examination object.

In at least one embodiment, the data processor of an embodiment of the a computed tomography system is further configured to:
compare data from the raw data set or data derived from the raw data set with trained data;
determine, based upon the compare, at least one correction variable; and
generate image data of the examination object using the at least one correction variable determined.

In at least one embodiment, a non-transitory computer program product stores a program, executable on a data processor, the executable program, following start-up and upon execution by the data processor, automatically carrying out the method of an embodiment.

In at least one embodiment, a non-transitory computer readable medium stores a program which, upon execution via a data processor, is configured to carry out the method of an embodiment.

BRIEF DESCRIPTION OF THE DRAWINGS

Example embodiments of the invention are explained in greater detail below on the basis of a schematic drawing, in which.

Parts Corresponding to One Another are Labeled with the same reference numerals in all the figures.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In at least one embodiment, the method is used for generating image data of an examination object, for example a patient, via a computed tomography system having a data processing unit, which computed tomography system has an X-ray radiation source and an X-ray radiation detector, which are suspended on a support and are mounted such that they are rotatable about a z-axis, and which computed tomography system has an examination table or patient table for supporting the examination object as well as a reference object arranged in a fixed position relative to the examination table.

The support of the X-ray radiation source and of the X-ray radiation detector is embodied here for example as what is known as a C-arm. Preferably, however, the support is embodied by a rotor of a gantry, so that the computed tomography system in this case has a gantry.

The data processing unit may be a processor, a control unit, a computer or a server, for example. According to a preferred embodiment variant, the computed tomography system has two data processing units, namely a first data processing unit and a second data processing unit, in other words for example one control unit and one computer, wherein then typically one part of the method according to the invention is carried out via the first data processing unit and another part of the method according to the invention via the second data processing unit.

In particular if the computed tomography system also has a gantry, then the first data processing unit, for example a control unit, is more preferably part of the gantry, while the second data processing unit, for example a computer or a server, is embodied as a physical unit at least spatially separate from the gantry and is or can be coupled to the gantry for example via a cable connection, a sliding contactor or a radio connection for the purpose of data exchange. In such a case, the second data processing unit is usually also set up in a different room from the gantry.

If the examination object is now positioned on the examination table, or table for short, then while the method according to at least one embodiment of the invention for generating a raw data set is being carried out, the X-ray radiation source as well as the X-ray radiation detector are displaced relative to the examination object and, during generation of the raw data set, at least one part of the examination object is sampled via X-ray radiation together with at least one part of the reference object. The sampling of the at least one part of the reference object is then used subsequently to at least partially compensate for the influence of movement errors, in other words in particular movement errors of the kind described in the introduction, during the displacement of the X-ray radiation source and the X-ray radiation detector relative to the examination object.

Here, the computed tomography system is typically embodied such that a (location) coupling of the kind described in the introduction is not provided or is provided at least to a lesser extent, so that movement errors, in other words in particular movement errors of the kind described in the introduction, can be expected, which significantly reduce the image quality that can be achieved for the image data of the examination object. During the spiral scan or spiral sampling, a relative movement therefore expediently continues to be realized, in which the X-ray radiation source and the X-ray radiation detector in each case traverse a spiral-shaped path at a highly constant speed, although the movement mechanism is typically less precise and therefore greater and/or more frequent deviations of the real relative positions from the required relative positions of an ideal spiral path are to be assumed.

Here, the computed tomography system preferably has a gantry, which is embodied as a freely displaceable or self-driven gantry and has for example wheels or a chain drive. This gantry is thus not then anchored but instead can be displaced freely relative to the ground system, in other words for example freely on a floor of an examination room. Here, it is also not usually bound to one room, in other words in particular an examination room, but can instead also be displaced for example between different examination rooms. Moreover, the gantry is preferably not positively driven, for example via rails. It is typically freely displaceable in two linearly independent and in particular orthogonal directions, and to this end has for example a carriage with wheels or with a chain drive. The linear movement in the direction of the z-axis or in the z-direction required for the spiral scan is then preferably carried out by the gantry, which for this purpose has a control unit, in other words in particular the aforementioned first data processing unit, with which a corresponding linear movement is carried out automatically during a spiral scan.

Here, such a linear movement takes place for example also on an uneven floor of an examination room, which then leads to relevant movement errors. In one way or another, greater and/or more frequent deviations of the real relative positions from the required relative positions of an ideal spiral path are typically to be assumed. The realized trajectory will therefore typically deviate more significantly from the ideal trajectory. The ideal trajectory nevertheless preferably continues to be used as the basis for generating the raw data set and calculating attenuation values for the voxels. However, the raw data set then additionally undergoes a post-processing, during which the influence of the movement errors is at least partially and preferably fully compensated for.

For the post-processing, preferably only data from the raw data set and data stored in a memory of the computed tomography system is used here, and more preferably the use of sensor data that is generated via an additional sensor apparatus for determining the relative positions on the basis of measurements is dispensed with. Here, the post-processing of the raw data set expediently takes place in the data processing unit of the computed tomography system and preferably in the aforementioned second data processing unit. The respective data processing unit then typically has an executable program, which following start-up automatically executes the corresponding method steps, in other words in particular the post-processing of the raw data set.

During the course of the post-processing, data from the raw data set or data derived from the raw data set is then preferably compared with trained data, in other words in particular with data stored in a data memory of the computed tomography system, and as a result a correction variable or correction variables is or are determined, which is or are used to generate image data of the examination object.

In an advantageous development, image data of the reference object is generated during the further processing or post-processing of the raw data set and typically before a generation of image data of the examination object based on the raw data set. According to a preferred embodiment variant, a number of sectional images of the reference object is generated here and then the image data corresponds accordingly to the number of sectional images.

More preferably, more than 5 sectional images and in particular more than 10 sectional images, in other words for example 20 sectional images, are generated or calculated here. The sectional images expediently comprise consecutive sections, so that the number of sectional images corresponds to a volume region of the reference object. Therefore, if for example 20 sectional images are generated with an image distance of 0.5 mm in each case, this represents a continuous object region of approximately 1 cm. It is furthermore considered expedient if the number of sectional images is less than 40 and in particular less than 30.

The generated image data of the reference object is then advantageously compared in an evaluation process with trained image data of the reference object, in other words in particular with image data stored in a memory. Here, what is known as a deep learning network or deep convolutional network is then used, for example, and an automatic image recognition or an automatic image comparison implemented. Corresponding systems are known from the prior art and are already used inter alia for image recognition. According to one embodiment variant, the image data of the reference object is supplemented with what is known as meta-information, in other words for example a time stamp, for the evaluation process and in particular for evaluation in a previously specified network.

Furthermore, correction variables are preferably determined with the aid of the image data comparison during a corresponding evaluation process and then more preferably a corrected raw data set is generated with the aid of these correction variables. Here, the correction variables represent for example the deviation of an actual trajectory from an ideal trajectory, wherein the actual trajectory corresponds to the movement of the X-ray radiation detector during the generation of the raw data set and thus during the spiral scan relative to the scanned volume of the reference object and to the scanned volume of the examination object, whereas the ideal trajectory corresponds to an idealized movement, in other words for example an ideal spiral path, along which the X-ray radiation detector moves at a constant speed.

Finally, image data and in particular sectional images of the examination object are preferably generated on the basis of the corrected raw data set.

The reference object used in this method is more preferably attached to the examination table, also referred to as patient table, and in particular a tabletop of the examination table. Here, the reference object is preferably positioned such that it is spatially separated from the examination object, in other words arranged at a certain distance from the examination object. This means that the examination object and the reference object preferably do not touch one another.

The reference object more expediently has a longitudinal axis. Here, the extent of the reference object in the direction of the longitudinal axis is usually greater than 20 cm, preferably greater than 30 cm and in particular greater than 50 cm or even greater than 100 cm.

Furthermore, the longitudinal axis of the reference object is typically aligned, in a close approximation, parallel to the longitudinal axis of the tabletop. Here, the longitudinal axis of the tabletop is expediently aligned, in an initial approximation, parallel to the z-axis during a spiral scan. This means that a self-driving gantry usually aligns itself automatically parallel to the longitudinal axis of the tabletop during a spiral scan and then moves in a direction parallel to the longitudinal axis of the tabletop, or that for example a self-driving gantry automatically moves in a direction parallel to the longitudinal axis of the tabletop during a spiral scan, provided that it has previously been aligned parallel to the longitudinal axis, for example by a user. The tabletop and in particular the examination table, on the other hand, are preferably not moved during a spiral scan and accordingly their positions and alignments relative to the ground system remain unchanged during a spiral scan.

It is also advantageous if the cross-section of the reference object at right angles to its longitudinal axis changes along the longitudinal axis. It is also expedient if the cross-section of the reference object at right angles to a transverse axis along the transverse axis, wherein the transverse axis is aligned perpendicularly to the longitudinal axis. If both is the case, then typically a fine three-dimensional structure is implemented.

Furthermore, the reference object has for example several torus-shaped or disk-shaped elements. Here, such an element has an extension of approximately 5 mm in the direction of the longitudinal axis of the reference object, for example. Depending on the embodiment variant, an intermediate space of 5 mm, for example, is left between two elements.

According to one embodiment, several elements furthermore have different diameters. Here, for example, a number of elements forms a group, in which the diameter viewed in the direction of the longitudinal axis of the reference object increases from element to element or decreases from element to element. Then, depending on the embodiment variant, group embodies the reference object or several groups, for example several identical groups, embody the reference object.

It is moreover advantageous if several elements have a protrusion or a depression, for example a groove, a through-hole or a blind hole. It is furthermore expedient if these protrusions or depressions are embodied differently and/or are positioned at different angular positions about the longitudinal axis of the reference object.

Here, the angular positions are preferably offset from element to element in a circumferential direction about the longitudinal axis, for example in each case by 5° or 10°, viewed in the direction of the longitudinal axis of the reference object so that the protrusions or depressions of all elements are arranged or positioned along a spiral path. Alternatively, the protrusion or depression is offset by a predetermined angle only at every third or every fourth element.

Figure 1:
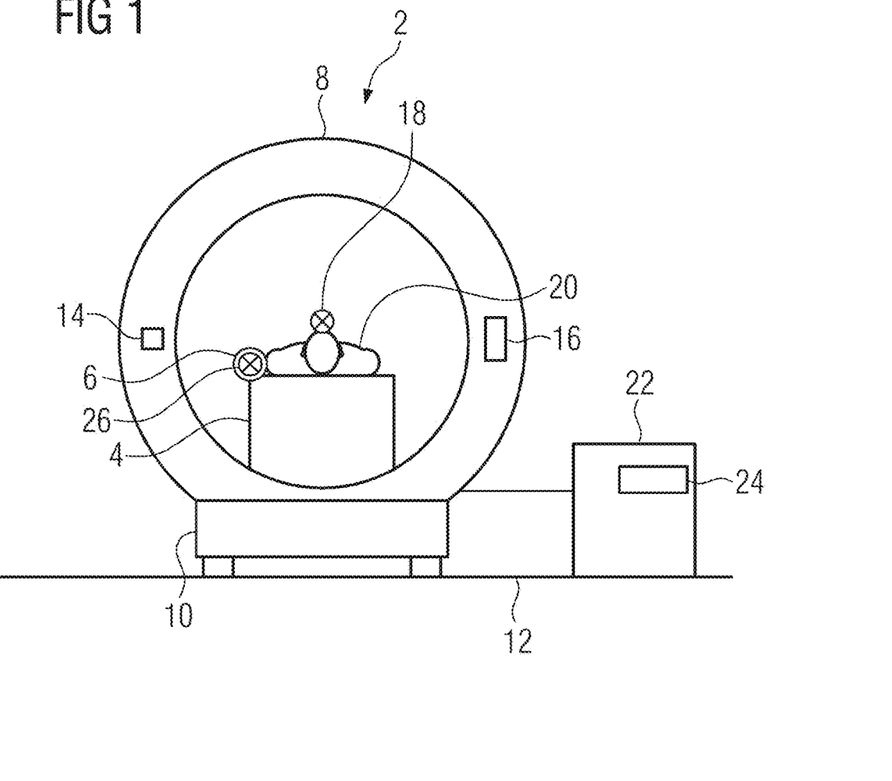
FIG. 1 shows a computed tomography system with a reference object in a front view.

A method described by way of example below is used to generate image data via a computed tomography system 2, as is represented schematically in FIG. 1.

Here, the computed tomography system 2 has an examination table 4 with a tabletop (not shown in detail). In the example embodiment, a reference object 6 is attached to this tabletop, which reference object extends along a longitudinal axis 26, which is aligned parallel to a longitudinal axis of the tabletop.

A further part of the computed tomography system 2 is a gantry 8, which is embodied as a self-driving gantry 8. Here, the gantry 8 in the example embodiment has a carriage 10 with wheels, with which the gantry 8 is freely displaceable on a floor 12 of an examination room. In the gantry 8, according to a principle which is known per se, an X-ray radiation source 14 on the one hand and an X-ray radiation detector 16 on the other hand are mounted such that they are rotatable about a z-axis 18, wherein the X-ray radiation source 14 and the X-ray radiation detector 16 are suspended opposite one another in a fixed position relative to one another and in a fixed alignment relative to one another in the gantry 8.

In order to carry out an examination of an examination object 20 and thus generate image data of the examination object 20, said examination object is positioned on the tabletop of the examination table 4 and subsequently sampled with X-ray radiation via a spiral scan. Here, in order to carry out the spiral scan, the X-ray radiation source 14 and the X-ray radiation detector 16 rotate about the z-axis 18 of the gantry 8 and furthermore the gantry 8, the z-axis 18 of which is aligned in an initial approximation parallel to the longitudinal axis of the tabletop, is displaced in a direction parallel to the longitudinal axis of the tabletop. During the spiral scan, the z-axis is thus aligned in an initial approximation parallel to the longitudinal axis of the tabletop and thus also to the longitudinal axis of the reference object 6.

Furthermore, the computed tomography system 2 has a data processing unit 22, which is embodied for example by a computer or a server and does not necessarily have to be arranged in the same room as the gantry 8 and the examination table 4.

Figure 2:
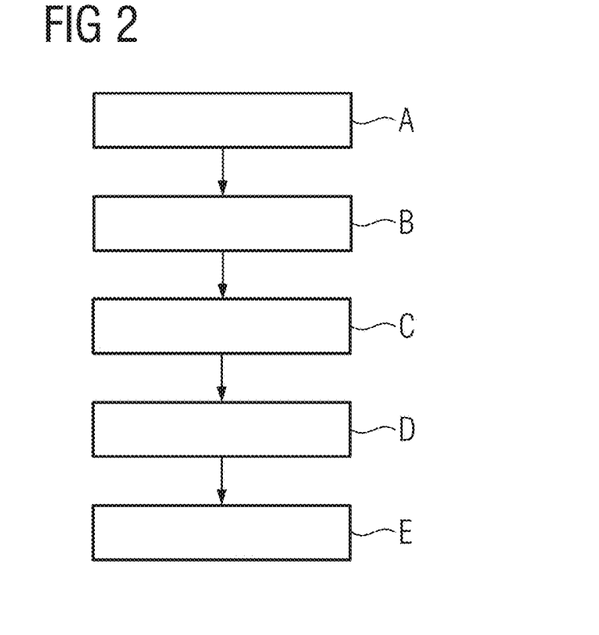
FIG. 2 shows a method for generating image data via the computed tomography system in a block diagram.

The method described here can be subdivided into several method steps or parts A to E, which run consecutively or are carried out consecutively in the example embodiment, as shown in FIG. 2. During the course of a first part A, a spiral scan is carried out and a raw data set generated. Here, at least one part of the examination object 20 is sampled together with at least one part of the reference object 6 during the spiral scan, so that the raw data set has information about the examination object 20 on the one hand and about the reference object 6 on the other hand.

This raw data set is used in a further part B of the method in order to generate or calculate image data of the reference object 6 on this basis, wherein in the example embodiment 20 sectional images form the image data. These sectional images represent consecutive sections of the reference object 6, which correspond for example to an approximately 1 cm long section of the reference object 6.

In a further method part C, an evaluation process, the image data of the reference object 6 thus determined is compared with trained image data, in other words image data stored in a memory 24 of the data processing unit 22, and correction variables are then determined with the aid of this comparison.

In a further part D of the method, these correction variables are used to generate a corrected raw data set, wherein the attenuation values assigned to the voxels undergo a correction based on the raw data set.

The corrected raw data set is then typically stored permanently, whereas the raw data set is usually no longer required and can therefore be deleted again and, in some cases, is also deleted. The corrected raw data set is then used in a further method part E in order to generate image data of the examination object 20, in other words in particular sectional images, on this basis.

A suitable reference object 6 for the method described above is sketched in FIG. 3 in a perspective view. In this example embodiment, the reference object 6 has a number of elements 28, which are all embodied to be substantially identical, here torus-shaped. In the example embodiment according to FIG. 3, the elements 28 are further arranged concentrically and concatenated along the longitudinal axis 26 of the reference object 6. Moreover, each element 28 has a depression 30, which is embodied in the manner of a blind hole in the example embodiment. In addition, as can be seen from FIG. 3, the angular positions of the depressions 30 vary about the longitudinal axis 26 of the reference object 6, wherein, viewed in the direction of the longitudinal axis 26, the angular positions are offset from element 28 to element 28 in steps of 5° or 10°, for example, in the circumferential direction about the longitudinal axis 26.

Figure 4:
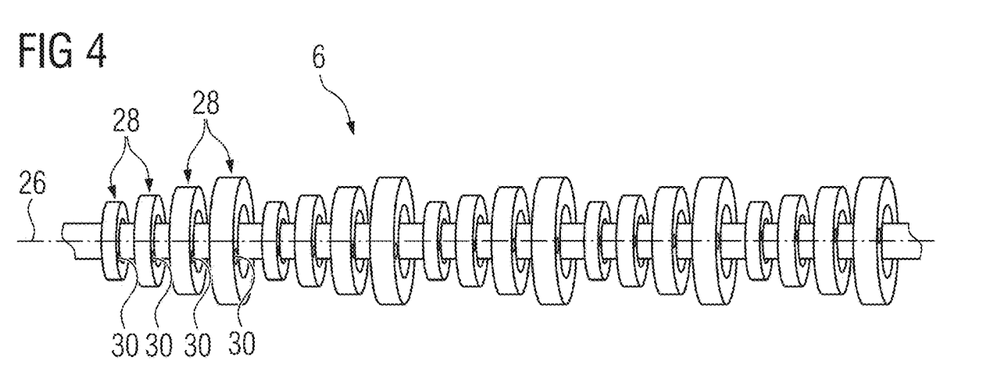
FIG. 4 shows a second embodiment of the reference object in a perspective view.

An alternative embodiment variant of the reference object 6 is shown in FIG. 4. In this example embodiment, four disk-shaped elements 28 embody a group and nine identical groups are concatenated in the longitudinal direction 26 of the reference object. The elements 28 of a group all have different diameters and the elements 28 are arranged within the group such that the diameter, viewed in the direction of the longitudinal axis 26, either increases or decreases from element 28 to element 28. Viewed across the groups, a periodic pattern is thus embodied by the different diameters of the elements 28. Furthermore, in the example embodiment according to FIG. 4, the elements 28 also have depressions 30, which are however embodied as through-holes. Furthermore, the depressions 30 of the elements 28 of a group have different diameters. The depressions 30 of the elements 28 of a group are however arranged at the same angular positions. The angular positions of the depressions 30 of two consecutive groups are however in turn offset, for example by 5° or 10°, in the circumferential direction about the longitudinal axis 26.

Figure 3:
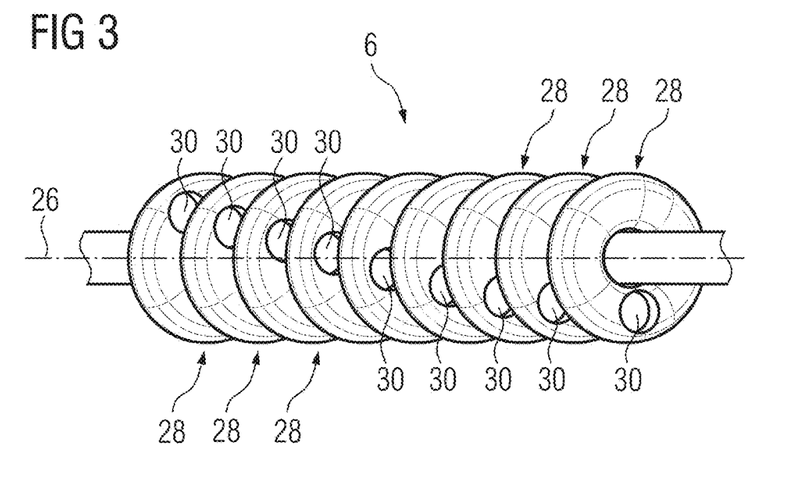
FIG. 3 shows a first embodiment of the reference object in a perspective view.

In both example embodiments, the elements 28, viewed in the direction of the longitudinal axis 26 of the reference object 6, have an extent of approximately 5 mm and a distance of approximately 5 mm, for example, is left between two elements 28.

On account of the selected structure of the reference object 6, it is possible by analyzing or evaluating image data of the reference object 6 to reach a conclusion regarding the realized trajectory or motion characteristic of the gantry 8 during the spiral scan and/or it is possible to determine or calculate a deviation from an ideal trajectory or an ideal motion characteristic, in other words for example a deviation from an ideal spiral path. Here, it is typically possible, for each point in time, to identify deviations in three spatial directions and also deviations in three directions of rotation, so that tilting of the gantry 8 during the spiral scan can also be determined by analyzing the image data of the reference object 6. As a result, an item of measurement hardware for determining the actual motion characteristic can for example be dispensed with and, according to one embodiment variant, is also dispensed with.

The invention is not limited to the example embodiment described above. Rather, other variants of the invention can also be derived herefrom by the person skilled in the art, without departing from the subject matter of the invention. In particular it is furthermore possible to combine all the individual features described in connection with the example embodiment with one another in a different way also, without departing from the subject matter of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating image data of an examination object via a computed tomography system including a processor, an examination table, and an X-ray radiation source and an X-ray radiation detector suspended on a support and mounted to be rotatable about a z-axis, the examination table to support the examination object and a reference object arranged in a fixed position relative to the examination table, the method comprising:
   generating a raw data set by displacing the X-ray radiation source and the X-ray radiation detector, relative to the examination object;
   sampling, via X-ray radiation during the generating of the raw data set, at least one part of the examination object together with at least one part of the reference object;
   compensating, at least in part, for an influence of movement errors during the displacing of the X-ray radiation source and the X-ray radiation detector relative to the examination object, wherein
      the compensating uses the sampling of the at least one part of the reference object, and
      the compensating includes
         generating image data of the reference object based on the raw data set, before generating the image data of the examination object,
         comparing, in an evaluation process, the image data of the reference object with trained image data of the reference object, and
         determining at least one correction variable based on the comparing;
   generating the image data of the examination object using the at least one correction variable.

2. The method of claim 1, wherein the image data of the reference object corresponds to a number of sectional images of the reference object.

3. The method of claim 1, wherein the compensating further comprises:
   generating, in a correction process, a corrected raw data set based on the raw data set and the at least one correction variable, and wherein the image data of the examination object is generated based on the corrected raw data set.

4. The method of claim 1, wherein a spiral scan is carried out to generate the raw data set.

5. The method of claim 1, wherein during the generating of the raw data set, the support, with the X-ray radiation source and the X-ray radiation detector, is displaced freely relative to the examination table.

6. The method of claim 1, wherein
   the reference object extends along a longitudinal axis, and
   a cross-section of the reference object, which is perpendicular to the longitudinal axis, varies along the longitudinal axis.

7. The method of claim 1, wherein the reference object includes a number of torus-shaped or disk-shaped elements.

8. A method for generating image data of an examination object via a computed tomography system including a processor, an examination table, and an X-ray radiation source and an X-ray radiation detector suspended on a support and mounted to be rotatable about a z-axis, the examination table configured to support the examination object and a reference object arranged in a fixed position relative to the examination table, the method comprising:
   generating a raw data set by displacing the X-ray radiation source and the X-ray radiation detector, relative to the examination object;
   sampling, via X-ray radiation during the generating of the raw data set, at least one part of the examination object together with at least one part of the reference object;
   compensating at least in part for an influence of movement errors during the displacing of the X-ray radiation source and the X-ray radiation detector relative to the examination object, wherein
      the compensating uses the sampling of the at least one part of the reference object,
      the reference object includes a number of torus-shaped or disk-shaped elements, and
      the torus-shaped or disk-shaped elements are arranged concentrically and concatenated along a longitudinal axis.

9. The method of claim 7, wherein at least some of the torus-shaped or disk-shaped elements differ in diameter.

10. The method of claim 7, wherein several of the torus-shaped or disk-shaped elements include a depression.

11. The method of claim 10, wherein
   the reference object extends along a longitudinal axis, and
   the depressions are positioned at different angular positions about the longitudinal axis.

12. A computed tomography system, comprising:
   an X-ray radiation source and an X-ray radiation detector, suspended on a support and mounted to be rotatable about a z-axis;
   an examination table to support an examination object and a reference object, the reference object arranged in a fixed position relative to the examination table; and
   a data processor configured to
      generate a raw data set upon displacing of the X-ray radiation source and the X-ray radiation detector relative to the examination object,
      sample, via X-ray radiation during generating of the raw data set, at least one part of the examination object together with at least one part of the reference object,
      compensate, at least in part, for an influence of movement errors, using the during the displacing of the X-ray radiation source and the X-ray radiation detector relative to the examination object, wherein
         the data processor is configured to compensate for the influence of movement errors using the sampling of the at least one part of the reference object, and
         the data processor is configured to compensate for the influence of movement errors by
            generating image data of the reference object based on the raw data set, before generating image data of the examination object, comparing, in an evaluation process, the image data of the reference object with trained image data of the reference object, and determining at least one correction variable based on the comparing, and generate the image data of the examination object using the at least one correction variable.

13. A non-transitory computer program product storing a program, executable on a data processor, the program, when executed on the data processor, causes the data processor to automatically carry out the method of claim 1.

14. The method of claim 3, wherein sectional images of the examination object are generated based on the corrected raw data set.

15. The computed tomography system of claim 12, wherein the computed tomography system is configured to perform a spiral scan is to generate the raw data set.

16. The computed tomography system of claim 12, wherein during generation of the raw data set, the support, with the X-ray radiation source and the X-ray radiation detector, is displaced freely relative to the examination table.

17. The computed tomography system of claim 12, wherein the reference object includes a number of torus-shaped or disk-shaped elements.

18. The computed tomography system of claim 17, wherein the torus-shaped or disk-shaped elements are arranged concentrically and concatenated along a longitudinal axis.

19. The computed tomography system of claim 17, wherein at least some of the torus-shaped or disk-shaped elements differ in diameter.

20. The computed tomography system of claim 17, wherein several of the torus-shaped or disk-shaped elements include a depression.

21. The computed tomography system of claim 20, wherein the reference object extends along a longitudinal axis, and the depressions are positioned at different angular positions about the longitudinal axis.

22. A non-transitory computer readable medium storing a program which, upon execution via a data processor, causes the data processor to carry out the method of claim 1.

23. The method of claim 7, wherein the torus-shaped or disk-shaped elements are arranged concentrically and concatenated along a longitudinal axis.

* * * * *